United States Patent [19]

Davis et al.

[11] Patent Number: 4,528,506
[45] Date of Patent: Jul. 9, 1985

[54] FERROMAGNETIC RESONANCE PROBE LIFTOFF SUPPRESSION APPARATUS

[75] Inventors: Thomas J. Davis, Issaquah; Paul L. Tomeraasen, West Richland, both of Wash.

[73] Assignee: The United States of America as represented by the Secretary of the Air Force, Washington, D.C.

[21] Appl. No.: 444,004

[22] Filed: Nov. 23, 1982

[51] Int. Cl.³ .................. G01N 27/82; G01R 33/12
[52] U.S. Cl. ............................... 324/225; 324/227; 324/237; 324/240
[58] Field of Search ............... 324/234–240, 324/225, 202, 226, 227, 232, 233

[56] References Cited

U.S. PATENT DOCUMENTS

| | | | |
|---|---|---|---|
| 3,197,693 | 7/1965 | Libby | 324/225 |
| 4,215,310 | 7/1980 | Schwerer | 324/225 |
| 4,286,216 | 8/1981 | Auld et al. | 324/235 X |
| 4,290,017 | 9/1981 | Fortunko | 324/237 |
| 4,340,861 | 7/1982 | Sparks | 324/202 X |
| 4,364,012 | 12/1982 | Auld | 324/237 |
| 4,383,218 | 5/1983 | Hansen et al. | 324/225 |
| 4,424,486 | 1/1984 | Denton et al. | 324/225 |

Primary Examiner—Gerard R. Strecker
Assistant Examiner—Warren S. Edmonds
Attorney, Agent, or Firm—Donald J. Singer; William Stephanishen

[57] ABSTRACT

A liftoff suppression apparatus utilizing a liftoff sensing coil to sense the amount a ferromagnetic resonance probe lifts off the test surface during flaw detection and utilizing the liftoff signal to modulate the probe's field modulating coil to suppress the liftoff effects.

5 Claims, 4 Drawing Figures

FERROMAGNETIC RESONANCE PROBE LIFTOFF SUPPRESSION APPARATUS

STATEMENT OF GOVERNMENT INTEREST

The invention described herein may be manufactured and used by or for the Government for governmental purposes without the payment of any royalty thereon.

BACKGROUND OF THE INVENTION

The present invention relates broadly to ferromagnetic resonance probes, and in particular to a liftoff suppression apparatus for a ferromagnetic resonance probe.

In the prior art, various methods to detect fatigue cracks to fastener holes and other critical areas of aircraft structural parts have become routine inspection requirements. Depending upon the acceptance limits established for inspection of hole cracks in a wing fitting for example, nondestructive test methods, techniques, and procedures are developed. X-rays are useful when gross cracks can be tolerated, or if accessibility is a problem. Ultrasonics can be used to detect cracks smaller than those found by X-rays, and when fasteners cannot be removed. Penetrants will detect cracks that are open to the surface, but are often times limited in their usefulness due to any foreign material embedded in a cracked area. Optical methods are extremely useful for showing small flaws, but extensive hole preparation is necessary in order to clean foreign materials and smeared metal from the hole surface. The methods for magnetic rubber and magnetic particle inspection of ferromagnetic parts have been developed utilizing soft iron indicators and electronic instruments to measure magnetic fields. While these methods are very desirable for inspection of steel parts, they are time consuming and require extensive surface preparation. Eddy currents inspection methods using both surface, and bolt hole probes, can detect not only small cracks, but requires a minimum of surface preparation. Because of these advantages, eddy currents are often selected as the primary inspection method.

Eddy current inspection techniques for nondestructive testing of fasteners holes and surface areas such as aircraft wing skins, and other structural parts requires that flaw information be obtained from probe contact to the material under test. Eddy current testing is based on the conductivity of the material which is primarily determined by the material's chemical composition. When a test coil is placed above the surface of an isolated conducting material, the coil's magnetic field induces current into the material. The eddy current field developed by the flow of eddy currents will vary as the flow of eddy currents varies. Cracks inclusions, and changes in conductivity will cause this flow to vary. This is accomplished by a hand held probe, or by using an automatic scanner which rotates the eddy current probe continuously 360° throughout the length of a fastener hole undergoing inspection. This automatic system makes use of the same general principles as mentioned above and has been established by hand-scan methods.

SUMMARY OF THE INVENTION

The present invention utilizes a ferromagnetic resonance probe in conjunction with a liftoff sensing coil and a bias field modulating coil to substantially reduce the probe to surface spacing or liftoff effect of the ferromagnetic resonance probe. The output of the liftoff sensing coil is utilized to modulate the bias field modulating coil thereby reducing the liftoff induced frequency shift in the ferromagnetic resonance probe's operating range.

It is one object of the present invention, therefore, to provide an improved liftoff suppression apparatus for the ferromagnetic resonance probe.

It is another object of the invention to provide an improved liftoff suppression apparatus wherein a sensing coil is utilized to provide liftoff correction signals.

It is another object of the present invention to provide an improved liftoff suppression apparatus wherein an approximately eight to one reduction on the liftoff induced frequency shift is achieved.

It is still another object of the present invention to provide an improved liftoff suppression apparatus wherein the sensitivity of the eddy current probe is increased due to the suppression of the liftoff effects.

These and other advantages, objects and features of the invention will become more apparent after considering the following description taken in conjunction with the illustrative embodiment in the accompanying drawings.

DESCRIPTION OF THE PREFERRED EMBODIMENT

Figure 1:
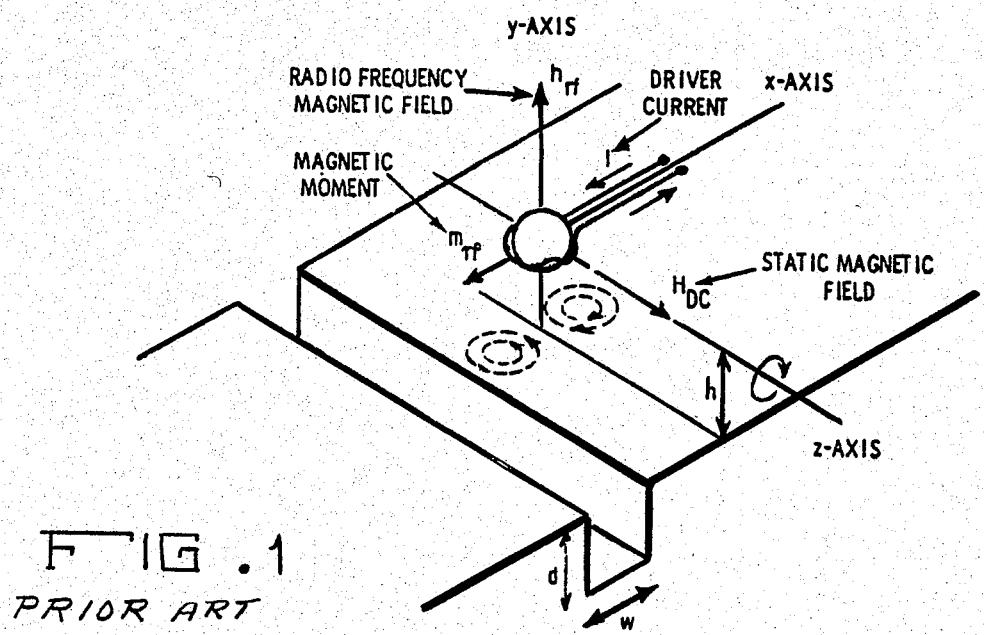
FIG. 1 is a schematic representation of a prior art ferromagnetic resonance probe.

There is shown in FIG. 1 a prior art ferromagnetic resonance probe which is capable of detecting small surface flaws in metals.

The active element in the ferromagnetic resonance (FMR) probe is a sphere of yttrium iron garnet (YIG) with a diameter on the order of 0.010 inch. The sphere is placed in a loop of wire so as to provide coupling to conventional microwave electronics. The resonant frequency of the sphere is determined not by its size but by the strength and direction of an applied DC magnetic field. Resonant frequencies in the range of 500 to 4000 MHz are attainable with the technique. The probe's magnetization precesses like a top about the applied DC field. A resonance mode known as uniform precession is the most useful and easiest to excite, and the precession processes uniformly about the DC field. When the probe is excited at a resonance, the rotating magnetic field links with adjacent materials and induces eddy currents in their surfaces. The level of eddy current activity (a function of both liftoff and flaw shape) affects the probe resonant frequency and the sharpness or "Q" of its resonance. These parameters which may be detected by suitable microwave frequency electronics are used as indicators of surface conditions. A high lateral resolution of flaws is obtained due to the small dimensions of the sphere and this is probably the most significant feature of the probe for non-destructive testing (NDT) applications.

Figure 2:
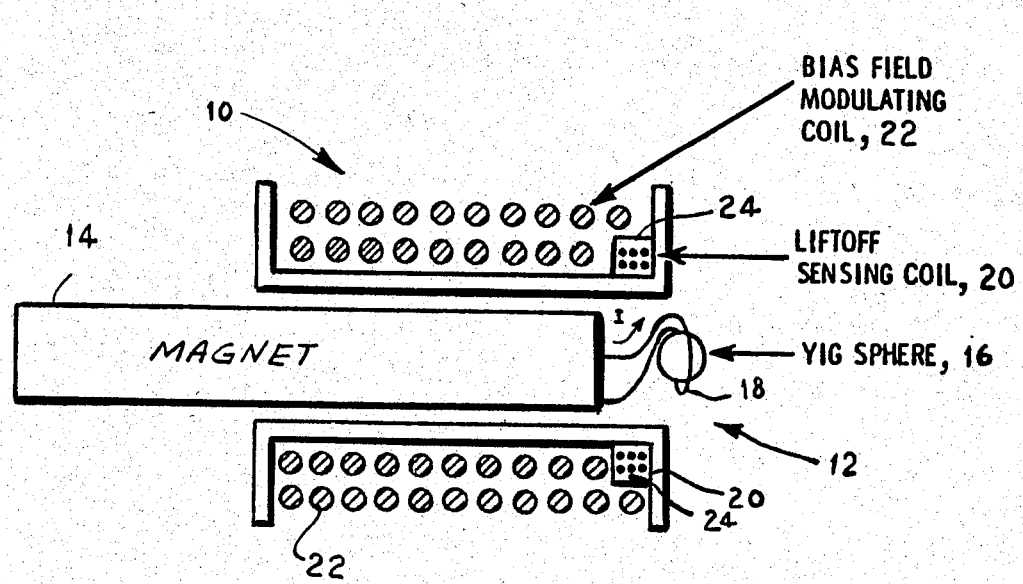
FIG. 2 is a partial sectional view of the liftoff suppression apparatus according to the present invention.

Referring to FIG. 2, there is shown a liftoff suppression apparatus 10 which is utilized in conjunction with a ferromagnetic resonance probe 12. The ferromagnetic resonance probe 12 comprises a magnet 14, a yttrium iron garnet (YIG) sphere 16, and a coupling loop 18. The coupling loop 18 provides a high frequency field $h_{rf}$ to the YIG resonator sphere 16 by means of the RF current, I, which flows through the loop 18. The static d.c. magnetic field $H_{dc}$ which is orthogonal to the magnetic field $h_{rf}$ (as shown in FIG. 1) is generated and applied by the magnet 14. A liftoff sensing coil 20 is located in close proximity to the YIG sphere 16. Since the liftoff sensing coil 20 projects a larger search field than the YIG sphere 16, it will be positioned as shown so that the sphere's microwave frequency field does not couple with it. The bias field modulating coil 22 which comprises a large electromagnet is then wound around and above the liftoff sensing coil 20 so that it will couple to the YIG sphere 16. It may be noted in FIG. 2 that the bias field modulating coil 22 is large or big in size as compared to the liftoff sensing coil 20. A slotted copper shield 24 is used to suppress coupling between the liftoff sensing coil 20 and the electromagnet 22.

Figure 3:
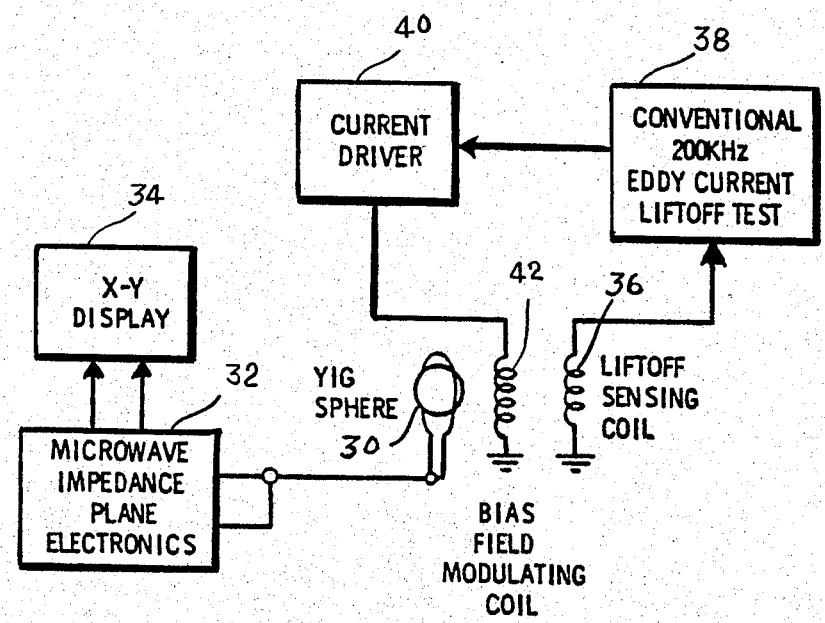
FIG. 3 is a block diagram of a test circuit utilizing the liftoff suppression apparatus, and, FIG. 4 is a graphical representation of the liftoff frequency shift versus probe liftoff.

Turning now to FIG. 3 there is shown a block diagram of a test circuit utilizing the liftoff suppression apparatus in conjunction with a ferromagnetic resonance probe. The YIG sphere 30 is driven by and provides surface flaw data to the microwave impedance plane electronics unit 32. The surface flaw data is applied to the x-y display unit 34 for display. The liftoff sensing coil 36 provides liftoff sense data to the eddy current liftoff test unit 38. The liftoff test unit 38 applies a liftoff signal to the current driver unit 40 which provides a liftoff correction signal to the bias field modulating coil 42. The conventional eddy current instrument operates the liftoff sensing coil at a test frequency of 200 kHz. The rotation control of the instrument is adjusted to place surface flaw responses in the horizontal output channel. The projection of the liftoff vector into the vertical output channel is then used as a flaw-free liftoff indication.

Figure 4:
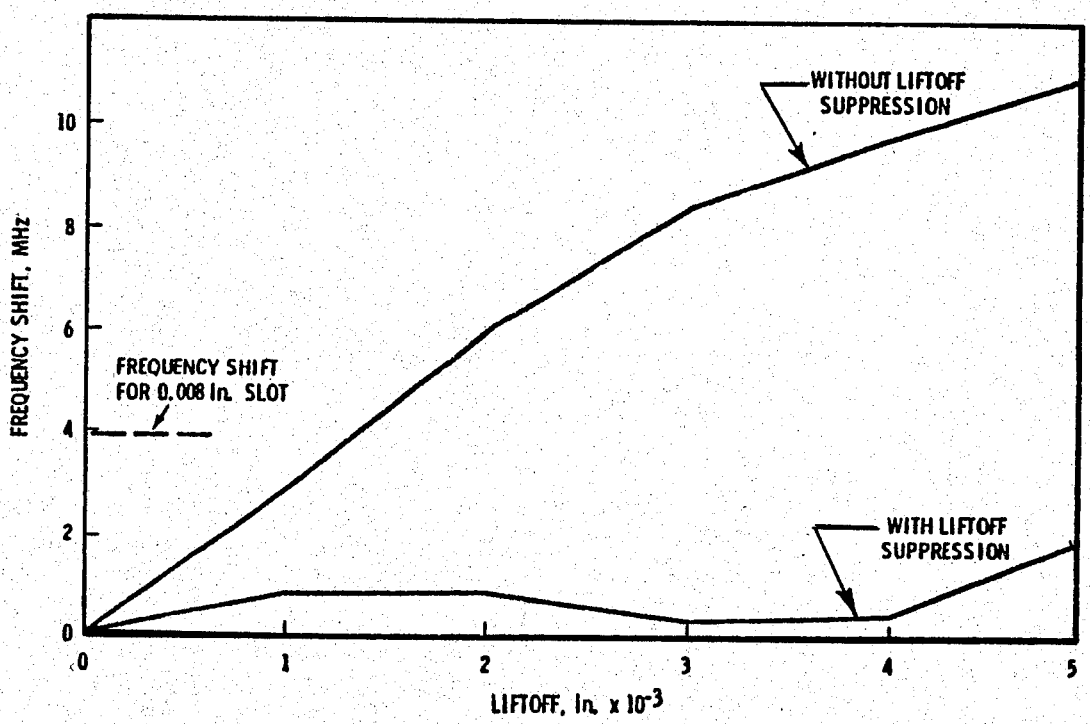

In FIG. 4 there is shown a graphical representation of the liftoff frequency shift versus probe liftoff for a ferromatic resonance probe with and without the liftoff suppression apparatus. The response of this liftoff suppression apparatus is shown in comparison to the normal (unsuppressed) response. Approximately an eight-to-one reduction of liftoff-induced frequency shift over the ferromagnetic resonance probe's usable range of liftoff is apparent in the suppressed data. Flaw sensitivity is unaffected by the technique, i.e., it diminishes with increasing liftoff as before.

Although the invention has been described with reference to a particular embodiment, it will be understood to those skilled in the art that the invention is capable of a variety of alternative embodiments within the spirit and scope of the appended claims.

What is claimed is:

1. A liftoff suppression apparatus for a ferromagnetic probe comprising in combination:
    a ferromagnetic resonance probe comprising a sphere of yttrium iron garnet, a loop wire in close proximity to and substantially surrounding said sphere to couple with but not in contact with said sphere, means for applying an RF current to said loop of wire, said ferromagnetic resonance probe having a microwave frequency associted therewith, and a magnet to apply a constant magnetic field to said sphere,
    a liftoff sensing coil located in close proximity to said sphere but not coupling with the microwave frequency field associated with said sphere due to the RF current flowing in said loop of wire around said sphere, said liftoff sensing coil measuring the amount of liftooof to said ferromagnetic resonance probe from the surface under test and providing a liftoff signal in proportion thereto,
    a means for measuring eddy currents, said eddy current measuring means receiving said liftoff signal from said liftoff sensing coil, said eddy current measuring means providing a current driver signal in response to said liftoff signal,
    a current driver means receiving said current driver signal from said eddy current measuring means, said current driver means generating a bias signal in response to said current driver signal, and,
    a bias field modulating coil positioned around said ferromagnetic resonance probe so that it will couple with said sphere, said bias field modulating coil receiving said bias signal from said current driver means, said bias signal modulating said bias field modulating coil to modulate the bias field of said ferromagnetic resonance probe so as to counteract the liftoff of said ferromagnetic resonance probe.

2. A liftoff suppression apparatus as described in claim 1 further including a microwave control means to generate said RF current for said ferromagnetic resonance probe and to detect changes in the resonant frequency of said ferromagnetic resonance probe, and
    a display means connected to said microwave control means to display the resonant frequency response of said ferromagnetic resonance probe.

3. A liftoff suppression apparatus as described in claim 2 wherein said bias field modulating coil comprises an electromagnet.

4. A liftoff suppression apparatus as described in claim 2 wherein said liftoff sensing coil comprises an eddy current sensing coil.

5. A liftoff suppression apparatus as described in claim 4 further including a slotted copper shield between said bias field modulating coil and said liftoff sensing coil.

* * * * *